(12) United States Patent
Ranka et al.

(10) Patent No.: US 7,553,983 B2
(45) Date of Patent: Jun. 30, 2009

(54) ORGANOSILICON COMPOUNDS

(75) Inventors: Ajay Ishwarlal Ranka, Gujarat (IN); Praksh Vithaldas Mehta, Gujarat (IN)

(73) Assignee: Zydex Industries, Gujarat (IN)

( * ) Notice: Subject to any disclaimer, the term of this patent is extended or adjusted under 35 U.S.C. 154(b) by 0 days.

(21) Appl. No.: 11/782,189

(22) Filed: Jul. 24, 2007

(65) Prior Publication Data

US 2008/0009644 A1    Jan. 10, 2008

Related U.S. Application Data

(63) Continuation-in-part of application No. 11/468,092, filed on Aug. 29, 2006, and a continuation-in-part of application No. 11/468,100, filed on Aug. 29, 2006, now Pat. No. 7,521,573.

(30) Foreign Application Priority Data

| Jul. 7, 2006 | (IN) | ...................... 1069/MUM/2006 |
| Jul. 7, 2006 | (IN) | ...................... 1070/MUM/2006 |
| Jun. 6, 2007 | (IN) | ...................... 1070/MUM/2007 |

(51) Int. Cl.
C07F 7/04    (2006.01)
(52) U.S. Cl. .................. 556/419; 556/413; 556/428; 556/449
(58) Field of Classification Search ................. 556/419, 556/413, 428, 449
See application file for complete search history.

(56) References Cited

U.S. PATENT DOCUMENTS

| 2,115,622 | A |   | 4/1938 | Dawson |
| 2,721,812 | A |   | 10/1955 | Iler |
| 3,352,894 | A |   | 11/1967 | Crain et al. |
| 3,560,385 | A |   | 2/1971 | Roth |
| 3,730,701 | A |   | 5/1973 | Isquith et al. |
| 3,772,062 | A |   | 11/1973 | Shur et al. |
| 3,794,736 | A |   | 2/1974 | Abbott et al. |
| 3,814,739 | A |   | 6/1974 | Takeda |
| 3,849,357 | A |   | 11/1974 | Wolf |
| 3,860,709 | A |   | 1/1975 | Abbott et al. |
| 3,879,206 | A |   | 4/1975 | Nestler et al. |
| 3,914,476 | A |   | 10/1975 | Nitzsche et al. |
| 3,955,985 | A |   | 5/1976 | Bosch et al. |
| 4,002,800 | A |   | 1/1977 | Nestler et al. |
| 4,005,028 | A | * | 1/1977 | Heckert et al. ............... 510/180 |
| 4,005,030 | A | * | 1/1977 | Heckert et al. ............... 510/180 |
| 4,005,119 | A | * | 1/1977 | Heckert et al. ............... 556/418 |
| 4,035,411 | A | * | 7/1977 | Heckert et al. ............... 556/413 |
| 4,209,432 | A |   | 6/1980 | Roth |
| 4,273,813 | A |   | 6/1981 | Meddaugh |
| 4,282,366 | A |   | 8/1981 | Eudy |
| 4,342,796 | A |   | 8/1982 | Brown |
| 4,390,712 | A |   | 6/1983 | Karl et al. |
| 4,408,996 | A |   | 10/1983 | Baldwin |
| 4,414,268 | A |   | 11/1983 | Baldwin |
| 4,417,066 | A |   | 11/1983 | Westall |
| 4,478,911 | A |   | 10/1984 | Price |
| 4,486,476 | A |   | 12/1984 | Fritsch |
| 4,504,541 | A |   | 3/1985 | Yasuda |
| 4,522,932 | A |   | 6/1985 | Mitchell, III |
| 4,601,902 | A |   | 7/1986 | Fridd et al. |
| 4,615,937 | A |   | 10/1986 | Bouchette |
| 4,631,207 | A |   | 12/1986 | Price |
| 4,648,904 | A |   | 3/1987 | De Pasquale |
| 4,692,374 | A |   | 9/1987 | Bouchette |
| 4,717,599 | A |   | 1/1988 | Merrill |
| 4,741,773 | A |   | 5/1988 | Kuroda |
| 4,753,977 | A |   | 6/1988 | Merrill |
| 4,786,531 | A |   | 11/1988 | Hodson |
| 4,845,256 | A |   | 7/1989 | Mebes |
| 4,846,886 | A |   | 7/1989 | Fey |
| 4,847,088 | A |   | 7/1989 | Blank |
| 4,865,844 | A |   | 9/1989 | Blank et al. |
| 4,874,431 | A |   | 10/1989 | Fey |
| 4,877,654 | A |   | 10/1989 | Wilson |
| 4,899,747 | A |   | 2/1990 | Garren |
| 4,908,355 | A |   | 3/1990 | Gettings et al. |
| 4,921,701 | A |   | 5/1990 | Blehm Blank |
| 4,985,023 | A |   | 1/1991 | Blank et al. |

(Continued)

FOREIGN PATENT DOCUMENTS

CA    2115622    9/1994

(Continued)

OTHER PUBLICATIONS

International Search Report for PCT Application No. PCT/IN2006/00304; Filed Aug. 22, 2006; Date of Completion Oct. 5, 2008; Date of Mailing Oct. 23, 2008.

(Continued)

*Primary Examiner*—Karl J. Puttlitz
*Assistant Examiner*—Chukwuma O Nwaonicha
(74) *Attorney, Agent, or Firm*—Alston & Bird LLP

(57) ABSTRACT

Transesterified organosilicon compounds, including ionic organosilicon compounds and coupling agents, and aqueous-based compositions including transesterified organosilicon compounds are provided. Compositions comprising at least one transesterified organosilicon are suitable for application to various inorganic, organic and cullulosic surfaces for imparting water repellency and improved wetting. Compositions comprising transesterified organosilicon compounds exhibit reduced flammability, improved hydrolytic stability, reduced gloss and improved water repellency while maintaining reactivity with various substrates.

9 Claims, No Drawings

U.S. PATENT DOCUMENTS

| | | | |
|---|---|---|---|
| 4,990,338 A | 2/1991 | Blank et al. | |
| 5,013,459 A | 5/1991 | Gettings et al. | |
| 5,019,173 A | 5/1991 | Gettings et al. | |
| 5,051,129 A | 9/1991 | Cuthbert et al. | |
| 5,073,195 A | 12/1991 | Cuthbert et al. | |
| 5,110,684 A | 5/1992 | Cooper | |
| 5,169,625 A | 12/1992 | Blank | |
| 5,209,775 A | 5/1993 | Bank et al. | |
| 5,300,327 A | 4/1994 | Stark-Kasley et al. | |
| 5,411,585 A | 5/1995 | Avery et al. | |
| 5,421,866 A | 6/1995 | Stark-Kasley et al. | |
| 5,695,551 A | 12/1997 | Buckingham et al. | |
| 5,798,144 A | 8/1998 | Varanasi et al. | |
| 6,376,696 B1 * | 4/2002 | Raab et al. | 556/423 |
| 6,482,969 B1 | 11/2002 | Helmrick et al. | |
| 6,803,152 B2 * | 10/2004 | Shembel et al. | 429/326 |
| 6,994,890 B2 | 2/2006 | Ohlhausen et al. | |

FOREIGN PATENT DOCUMENTS

| | | | |
|---|---|---|---|
| EP | 0355765 | | 2/1990 |
| GB | 1386876 | * | 4/1973 |
| JP | 3159975 | | 7/1991 |
| WO | WO 00/72850 | | 12/2000 |

OTHER PUBLICATIONS

Written Opinion for PCT Application No. PCT/IN2006/00304; Filed Aug. 22, 2006; Date of Completion Oct. 5, 2008; Date of Mailing Oct. 23, 2008.

* cited by examiner

ORGANOSILICON COMPOUNDS

CROSS-REFERENCE TO RELATED APPLICATIONS

This application is a continuation-in-part of U.S. patent application Ser. Nos. 11/468,092 and 11/468,100 both filed on Aug. 29, 2006, now U.S. Pat. No. 7,521,573, which claim priority to Indian Patent Application Nos. 1069/MUM/2006 and 1070/MUM/2006, respectively, both filed in India on Jul. 7, 2006, all of which are hereby incorporated herein in their entirety by reference. This application claims priority to Indian Patent Application No. 1070/MUM/2007 filed on Jun. 6, 2007.

BACKGROUND OF THE INVENTION

This invention relates to organosilicon compounds and compositions thereof, wherein at least one alkoxy group has been transesterified with a diol. Compositions including transesterified organosilicon compounds exhibit improved hydrolytic stability and are suitable for imparting water repellency to various surfaces.

The use of organosilicon compounds as water repellants is well known in the art. The organosilicon compounds known and practiced in the art include ethoxy and methoxy functional groups attached to the silicon moiety. These compounds are typically supplied as a 100% concentrate or diluted in an appropriate solvent. Prior organosilane compositions are sensitive to hydrolysis in presence of moisture, which undesirably leads to the generation of ethanol or methanol during storage, transportation and use. Accordingly, the generation of methanol or ethanol undesirably lowers the flash point of these products and inherently increases the hazards of using these products.

Many organosilicon compositions are simply diluted in water and applied to various inorganic surfaces. It is often observed that during the hydrolysis of the silane-alkoxy groups, the resulting silanol groups produced in-situ participate in intermolecular or intramolecular condensation with the substrate. See E. P. Plueddemann, Adhesion Through Silane Coupling Agent., J. Adhe. 2, 184 (1970), E. P. Plueddemann, Silane Coupling Agents for high temperature resins, Soc, Plast. Ind. RPC Proc. 22, 9A (1967). E. P. Plueddemann, Cationic Organofunctional Silane coupling agents, Soc, Plast. Ind. RPC Proc. 27, 21B (1972). However, such intermolecular condensation needs to be avoided in order to achieve optimum performance. See Barry Arkles, Chemtech, Vol. 7 (1977). Therefore, it would be desirable to have oganosilicon compositions that are non-flammable, hydrolytically stable and exhibit reduced intermolecular condensation while also being suitable for imparting water repellency and surface modification.

BRIEF SUMMARY OF THE INVENTION

This invention is directed to transesterified organosilicon compounds, including ionic organosilicon compounds and organo-functional silicon compounds, and aqueous-based compositions including transesterified organosilicon compounds. Compounds and compositions in accordance with embodiments of the present invention are suitable for application to various inorganic, organic and cellulosic surfaces for imparting water repellency, improved wetting and surface modification. Surprisingly it has been found that if at least one of the silane-alkoxy groups (e.g. methoxy or ethoxy) is transesterified with a diol, such as ethylene glycol, the organosilicon exhibits resistance to further hydrolysis, maintains a higher flash point and simultaneously exhibits reduced intermolecular condensation when mixed with water.

Although desiring not to be held to the following explanation, it is believed that the first alkoxy group which gets transesterified with a diol is the least sterically hindered group which then has an enveloping or shielding effect on the other two alkoxy groups. This shielding effect essentially reduces the rate of hydrolysis of the other alkoxy groups from further hydrolysis, which ultimately leads to substantially stable alkoxy groups during storage and transportation. Furthermore, it is believed that when the transesterified organosilicon compounds are mixed with water, the alkoxy groups such as methoxy and ethoxy groups are hydrolyzed and form silanol group that remain stable due to the slow hydrolyzing group, such as glycolether, substituted onto the organosilicon during the transesterification reaction. Accordingly, the presence of a glycolether group, for example, on a hydrolyzed silicon molecule significantly slows down intermolecular condensation reactions in an aqueous-based environment.

DETAILED DESCRIPTION OF THE INVENTION

The present invention now will be described more fully hereinafter, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements.

It is well established that in organosilane chemistry, a silane-alkoxy group (i.e. Si—OR) is known as a silane ester. Equally well known in the art of organosilane chemistry, a transesterification reaction is an exchange reaction in which two different alkoxy groups are exchanged with each other. For example, if Si—OCH$_3$ is reacted with HOCH$_2$CH$_2$OH the methoxy group is exchanged with glycol ether resulting in the formation of Si—OCH$_2$CH$_2$OH by the transesterification reaction.

Embodiments of the present invention are produced by reacting an organosilicon compound with a diol in the presence of heat to facilitate a transesterification reaction for the replacement of one or two alkoxy groups of the organosilicon. The diol can be variably supplied in excess depending on the need of the final composition. Final products, in accordance with various embodiments of the present invention, are suitable for imparting water repellency and for changing the surface characteristics of organic, inorganic or cellulosic surfaces. For example, transesterified organosilicons and compositions comprising transesterified compounds are especially useful as water-proofing agents, adhesion promoters and other traditionally known uses for organosilicon compounds and compositions thereof.

In one embodiment of the present invention, the transesterified organosilicon comprises an ionic organosilicon including compounds having a formula selected from the group consisting of:

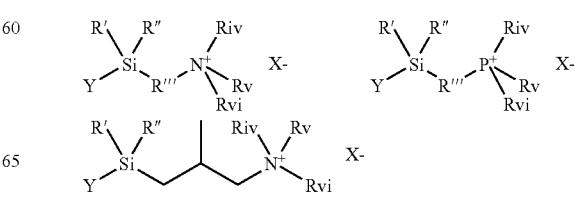

-continued

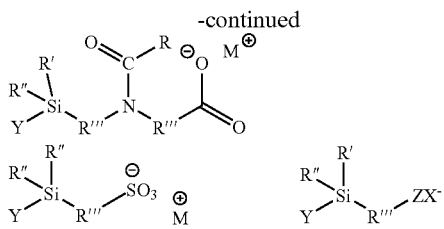

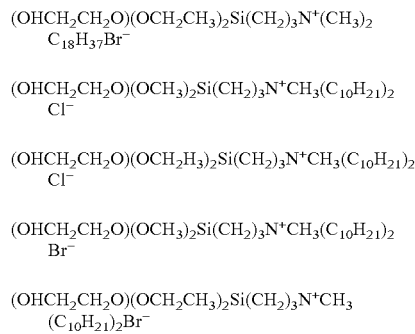

where in each formula:
Y is $(OCH_2CH_2)_nOH$ radical where n has a value of one through ten, or $[OC_3H_6]_nOH$ (propylene glycol) radical where n has a value of one through ten, or $[C_3H_7O_3]$ (glycerol) radical; R' is an alkyl radical including one to three carbons, or $(OCH_2CH_2)_nOH$ radical where n has a value of one through ten, or $[OC_3H_5]_nOH$ (propylene glycol) radical where n has a value of one through ten, or $[C_3H_7O_3]$ (glycerol) radical, or $[O(CH_2)_mCH_3]$ radical where m has a value of 0, 1, 2 or 3, or $(CH_3OCH_2CH_2O)$ radical, or $(CH_3CH_2OCH_2CH_2O)$ radical; R" is an alkyl radical including one to three carbons, or $[O(CH_2)_mCH_3]$ radical where m has value 0, 1, 2 or 3 or $(CH_3OCH_2CH_2O)$ radical, or $(CH_3CH_2OCH_2CH_2O)$ radical; R'" is an alkylene group including one to four carbon atoms; $R^{iv}$, $R^v$ and $R^{vi}$ are alkyl groups including one to twenty two carbon atoms wherein at least one such group is larger than eight carbon atoms, $-CH_2C_6H_5$, $-CH_2CH_2OH$, $-CH_2OH$, and $-(CH_2)_xNHC(O)R^{vii}$ wherein x has a value of from two to ten and $R^{vi}$ is a perfluoroalkyl radical having one to twelve carbon atoms; X is chloride, bromide, fluoride, iodide, acetate or tosylate; Z is a positively charged aromatic pyridinium ring of formula $C_5H_5N^+$; and M is Na, K, or Li or H.

In one alternative embodiment, the transesterified organosilicon comprises an ionic organosilicon selected from the formula:

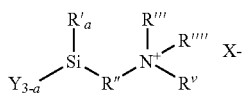

wherein Y is $(OCH_2CH_2)_nOH$ radical where n has a value of one through ten, or $[OC_3H_5]_nOH$ (propylene glycol) radical where n has a value of one through ten, or $[C_3H_7O_3]$, (glycerol) radical; a has a value of zero, one or two; R' is an alkyl radical including one to three carbons, or $[O(CH_2)_mCH_3]$ radical where m has value 0, 1, 2 or 3 or $(CH_3OCH_2CH_2O)$ radical, or $(CH_3CH_2OCH_2CH_2O)$ radical; R" is an alkylene group including one to four carbon atoms; R'" is methyl or ethyl; R"" and $R^v$ are alkyl groups containing one to twenty two wherein at least one such group is larger than eight carbon atoms and X is chloride, acetate or tosylate.

A non-exhaustive list of specific examples of transesterified organosilicon compounds within the scope of the present invention are represented by the formulas:

$(OHCH_2CH_2O)(OCH_3)_2Si(CH_2)_3N^+(CH_3)_2$
  $C_{18}H_{37}Cl^-$ $(OHCH_2CH_2O)(OCH_2CH_3)_2Si(CH_2)_3N^+(CH_3)_2$
  $C_{18}H_{37}Cl^-$ $(OHCH_2CH_2O)(OCH_3)_2Si(CH_2)_3N^+(CH_3)_2$
  $C_{18}H_{37}Br^-$ $(OHCH_2CH_2O)(OCH_2CH_3)_2Si(CH_2)_3N^+(CH_3)_2$
  $C_{18}H_{37}Br^-$ $(OHCH_2CH_2O)(OCH_3)_2Si(CH_2)_3N^+CH_3(C_{10}H_{21})_2$
  $Cl^-$ $(OHCH_2CH_2O)(OCH_2H_3)_2Si(CH_2)_3N^+CH_3(C_{10}H_{21})_2$
  $Cl^-$ $(OHCH_2CH_2O)(OCH_3)_2Si(CH_2)_3N^+CH_3(C_{10}H_{21})_2$
  $Br^-$ $(OHCH_2CH_2O)(OCH_2CH_3)_2Si(CH_2)_3N^+CH_3(C_{10}H_{21})_2Br^-$ $(OHCH_2CH_2O)(OCH_3)_2(CH_2)_3N^+(CH_3)_2$
  $CH_2C_6H_5Cl^-$ $(OHCH_2CH_2O)(OCH_2CH_3)_2Si(CH_2)_3N^+(CH_3)_2$
  $CH_2C_6H_5Cl^-$ $(OHCH_2CH_2O)(OCH_2CH_3)_2Si(CH_2)_3N^+(CH_3)_2$
  $C_{18}H_{37}Cl^-$ $(OHCH_2CH_2O)(OCH_3)_2Si(CH_2)_3N^+(CH_3)_2(CH_2)_3$
  $NHC(O)(CF_2)_6CF_3Cl^-$ $(OHCH_2CH_2O)(OCH_2CH_3)_2Si(CH_2)_3N^+(CH_3)_2$
  $(CH_2)_3NHC(O)(CF_2)_6CF_3Cl^-$

In yet another alternative embodiment, the transesterified organosilicon compound may be selected from the formula:

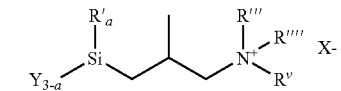

wherein Y is $(CH_2CH_2O)_nOH$ radical where n has a value of one through ten, $(CH_3OCH_2CH_2O)$, or $(CH_3CH_2OCH_2CH_2O)$ radical or $[OC_3H_6]_nOH$ (propylene glycol) radical where n has a value of one through ten, or $[C_3H_7H_3]$, (glycerol) radical; a has a value of one or two; R' is an alkyl radical including one to three carbons, or $[O(CH_2)_m CH_3]$ radical where m has value 0, 1, 2 or 3, or $(CH_3OCH_2CH_2O)$ radical, or $(CH_3CH_2OCH_2CH_2O)$ radical; R'", R"" and $R^v$ are alkyl groups containing one to twenty two carbon atoms wherein at least one such group is larger than eight carbon atoms, $-CH_2C_6H_5$, $-CH_2CH_2OH$, $-CH_2OH$, and $-(CH_2)_xNHC(O)R^{vii}$ wherein x has a value of from two to ten and $R^{vi}$ is a perfluoroalkyl radical having one to twelve carbon atoms; and X is chloride, bromide, fluoride, iodide, acetate or tosylate.

Specific examples of such transesterified organosilicon compounds within the scope of the present invention include, but are not limited to the following:

$(OHCH_2CH_2O)(OCH_3)_2SiCH_2CH(CH_3)CH_2N^+$
  $(CH_3)_2$ $C_{18}H_{37}Cl^-$ $(OHCH_2CH_2O)(OCH_2CH_3)_2SiCH_2CH(CH_3)CH_2N^+$
  $(CH_3)_2C_{18}H_{37}Cl^-$ $(OHCH_2CH_2O)(OCH_3)_2SiCH_2CH(CH_3)CH_2N^+$
  $(CH_3)_2$ $C_{18}H_{37}Br^-$ $OHCH_2CH_2O)(OCH_2CH_3)_2SiCH_2CH(CH_3)CH_2N^+$
  $(CH_3)_2C_{18}H_{37}Br^-$ $(OHCH_2CH_2O)(OCH_3)_2CH_2CH(CH_3)CH_2N+CH_3$
  $(C_{10}H_{21})_2Cl^-$ (OHCH₂CH₂O)(OCH₂CH₃)₂SiCH₂CH(CH₃)CH₂N+
CH₃(C₁₀H₂₁)₂Cl⁻

(OHCH₂CH₂O)(OCH₃)₂SiCH₂CH(CH₃)CH₂N⁺CH₃
(C₁₀H₂₁)₂Br⁻

(OHCH₂CH₂O)(OCH₂CH₃)₂SiCH₂CH(CH₃)CH₂N⁺
CH₃(C₁₀H₂₁)₂Br⁻

(OHCH₂CH₂O)(OCH₃)₂SiCH₂CH(CH₃)CH₂N⁺
(CH₃)₂ CH₂C₆H₅Cl⁻

(OHCH₂CH₂O)(OCH₂CH₃)₂SiCH₂CH(CH₃)CH₂N⁺
(CH₃)₂CH₂C₆H₅Cl⁻

(OHCH₂CH₂O)(OCH₃)₂SiCH₂CH(CH₃)CH₂N⁺
(CH₃)₂ (CH₂)₃NHC(O)(CF₂)₆CF₃Cl⁻

OHCH₂CH₂O)(OCH₂CH₃)₂SiCH₂CH(CH₃)CH₂N⁺
(CH₃)₂(CH₂)₃NHC(O)(CF₂)₆CF₃Cl⁻

In another alternative embodiment, the transesterified organosilicon compound may be selected from the formula:

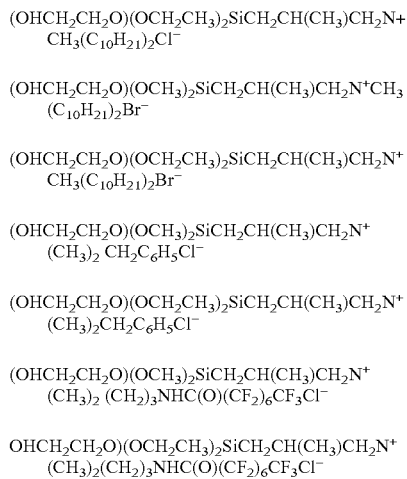

wherein Y is $(CH_2CH_2O)_nOH$ radical where n has a value of one through ten, $(CH_3OCH_2CH_2O)$, or $(CH_3CH_2OCH_2CH_2O)$ radical or $[OC_3H_6]_nOH$ (propylene glycol) radical where n has a value of one through ten, or $[C_3H_7O_3]$, (glycerol) radical; a has a value of one or two; R' is an alkyl radical including one to three carbons, or $[O(CH_2)_m CH_3]$ radical where m has value 0, 1, 2 or 3 or $(CH_3OCH_2CH_2O)$ radical, or $(CH_3CH_2OCH_2CH_2O)$ radical; R''', R'''' and R$^v$ are alkyl groups containing one to twenty two carbon atoms wherein at least one such group is larger than eight carbon atoms, —CH₂C₆H₅, —CH₂CH₂OH, —CH₂OH, and —(CH₂)ₓNHC(O)R$^{vii}$ wherein x has a value of from two to ten and R$^{vi}$ is a perfluoroalkyl radical having one to twelve carbon atoms; and X is chloride, bromide, fluoride, iodide, acetate or tosylate.

In another embodiment of the present invention, the transesterified organosilicon comprises an organosilane including compounds selected from the formula:

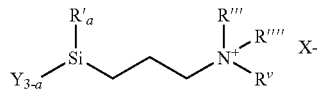

where X is $(OCH_2CH_2)_nOH$ radical where n has a value of one through ten or $[OC_3H_5]_nOH$ (propylene glycol) radical where n has a value of one through ten, or $[C_3H_7O_3]$, (glycerol) radical; m has value 1 or 2; R' is an alkyl group including one to three carbons or $(OCH_2CH_2)_nOH$ radical where n has a value of one through ten or $[OC_3H_5]_nOH$ (propylene glycol) radical where n has a value of one through ten, or $[C_3H_7O_3]$ (glycerol) radical, or $CH_2=CH_2$ radical, $OCH_3$, $OCH_2CH_3$ or $OC_3H_5$ radical or $(CH_3OCH_2CH_2O)$ or $(CH_3CH_2OCH_2CH_2O)$ radical; R'' is an alkyl group including one to three carbons or $(OCH_2CH_2)_nOH$ radical where n has a value of one through ten or $[OC_3H_5]_nOH$ (propylene glycol) radical where n has a value of one through ten, or $[C_3H_7O_3]$, (glycerol) radical, or $CH_2=CH_2$ radical, $OCH_3$, $OCH_2CH_3$ or $OC_3H_5$ radical or $(CH_3OCH_2CH_2O)$, or $(CH_3CH_2OCH_2CH_2O)$ radical; R''' is an alkylene group including one to four carbon atoms or perfluoroalkyl radical having one to twelve carbon atoms; Y is an organofunctional group including $NH_2$, $(CH_3)NH$, $(CH_3)_2N$, $NH_2CH_2CH_2NH$, $NH_2CH_2CH_2NHCH_2CH_2NH$, Cl, Br, F, I, CN, Methacryloxy, Glycidoxy, Acetoxy, H or HS.

Specific examples of transesterified organosilanes in accordance with various embodiments of the present invention include, but are not limited to the following:
3-Methacryloxypropyl(2-hydroxyethoxy)dimethoxysilane;
3-Glycidoxypropyl(2-hydroxyethoxy)dimethoxysilane;
3-Methacrloxypropyl(2-hydroxyethoxy)diethoxysilane;
3-Glycidoxypropyl(2-hydroxyethoxy)diethoxysilane;
Vinyl(2-hydroxyethoxy)dimethoxysilane;
Vinyl(2-hydroxyethoxy)diethoxysilane;
N-methylaminopropyl(2-hydroxyethoxy)dimethoxysilane;
N-methylaminopropyl(2-hydroxyethoxy)diethoxysilane;
N—N-dimethylaminopropyl(2-hydroxyethoxy) dimethoxysilane;
N—N-dimethylaminopropyl(2-hydroxyethoxy)diethoxysilane;
n-Octyl (2-hydroxyethoxy)diethoxysilane;
isobutyl (2-hydroxyethoxy)dimethoxysilane; and
isobutyl (2-hydroxyethoxy)diethoxysilane.

Compositions in accordance with embodiments of the present invention can be made by mixing or dissolving at least one transesterified orgaonsilicon compound in water. In one embodiment of the present invention, an aqueous composition can comprise a mixture of at least one transesterified ionic organosilicon compound and at least one transesterified organo-functional silicon compound. Furthermore, compositions in accordance with various embodiments of the present invention can include traditionally known excipients. For example, aqueous-based compositions of the present invention may optionally include a variety of known wetting agents, surfactants, buffering agents, and antimicrobial agents. As such, one embodiment of the present invention comprises a solution comprising at least one transesterified organosilicon and optionally comprising any combination of well-known excipients to further tailor the composition for a specific application. In an alternative embodiment, the present invention comprises an aqueous-based emulsion comprising at least one transesterified organosilicon and optionally comprising any combination of well-known excipients to further tailor the composition for a specific application. Additionally, embodiments of the present invention may comprise an aqueous-based solution or emulsion consisting essentially of at least one transesterified organosilicon. Compositions according to embodiments of the present invention can be applied to a wide variety of surfaces by any known means including for example by brush, roller, air spray, and airless spray techniques.

Any surface with functional groups that will bond with the silanols created by hydrolysis of the silane alkoxy groups may be rendered water repellant upon treatment with aqueous compositions of the present invention. Some suitable surfaces for example include heavy and light weight concrete, masonry products, gypsum, concrete blocks, cinder blocks, soft mud bricks, sand lime bricks, drain tiles, ceramic tiles, sandstone, plaster, clay bricks, natural stones and rocks, roofing tiles, calcium silicate bricks, cement articles, slag stones and bricks, stucco, limestone, macadam, marble, grouts, mortar, terrazzo, clinker, pumice, terra, cotta, porcelain, adobe, coral, dolomite sand and aggregates. Non-cement surfaces may be treated with compositions of the present invention including but not limited to perlite, cellular glass, vermiculite, mica, silica and diatomaceous earth. After an aqueous-based composition according to embodiments of the present invention is applied and allowed to dry, a treated surface is obtained comprising a protective water resistant layer bonded to the substrate.

Aqueous-based compositions according to one embodiment of the present invention comprises at least about 0.1 weight percent of at least one transesterified organosilicon compound. Additionally, some embodiments may comprise from about 0.1 to about 10 weight percent of at least one transesterified organosilicon compound while others may comprise between about 5 to about 95 weight percent or about 10 and 70 weight percent. In one alternative embodiment, the aqueous-based composition comprises from about 20 to about 60 weight percent of at least one transesterified organosilicon compound or from about 30 to about 50 weight percent or of at least one transesterified organosilicon compound.

EXAMPLE 1

3-(trimethoxysilyl)propyloctadecyldimethyl ammonium chloride in Ethylene glycol (hereinafter "Product II")

A two liter, three-necked flask equipped with a condenser, stirrer, thermometer and a distillation head, was charged with 360 grams (six moles) of ethylene glycol. Next, 315 grams of a 70% solution of methanol containing 3-(trimethoxysilyl) propyloctadecyl-dimethyl ammonium chloride (hereinafter "Product I") was added to the flask. The mixture was slowly heated under vacuum to 80° C. and free methanol 80 grams was distilled. The resulting composition was Product II.

EXAMPLE 2

3-[(2-hydroxyethoxy)dimethoxysilyl]propyldimethyloctadecyl ammonium chloride (hereinafter "Product III")

The product solution (i.e. Product II) from example 1 was further heated to 120° C. under vacuum. The reaction was allowed to continue. The transesterification resulted in methanol liberation which was removed and condensed. After 16 grams of methanol (0.5 mole) was collected, vacuum was released and cooling was applied. The average structure of the components of the crude product mixture in ethylene glycol was $(OCH_3)_2(OCH_2CH_2OH)SiCH_2CH_2CH_2N^+(CH_3)_2(C_{18}H_{37})Cl^-$, namely 3-[(2-hydroxyethoxy) dimethoxysilyl]propyldimethyloctadecyl ammonium chloride (i.e. Product III).

EXAMPLE 3

Flash Point Evaluation

Products I, II and III were each subjected to a flash point test. The results are summarized in Table-1. Each product was then heated to 80° C. for 4 days to simulate long storage life and subjected to a second flash point determination. The results are summarized in Table-1. The data provided in Table-1 demonstrates that Product III, namely the transesterified orgaonsilicon, not only exhibited a higher flashpoint than the comparative products but also did not exhibit any reduction in flash point upon aging at 80° C. for four days.

TABLE 1

| Sample | Flash Point* (° C.) | Flash Point (° C.) after Aging* |
|---|---|---|
| Product I | 15 | 15 |
| Product II | 105 | 25 |
| Product III | 105 | 105 |

*Flash Points measured using Pensky-Martin Closed-cup

EXAMPLE 4

Turbidity Analysis

It is well known in the art that intermolecular condensation of water soluble orgaonisilicon compounds cause solutions thereof to become cloudy and thus exhibit an increased level of turbidity. Specifically, an increase in clouding or milkiness of an aged solution is an interpretation of the extent of intermolecular condensation. Products I, II, and III were added to water in the proportion of 1:10 and maintained at a room temperature of approximately 30° C. for 7 days. The prepared aqueous solutions were monitored for an increased turbidity level. The results are summarized in Table-2. Unlike Products I and II, Product III (i.e. containing a transesterified organosilicon) exhibited a substantial improvement in shelf-life by maintaining a clear solution for around 150 hours. End-users find this property desirable for a variety of applications.

TABLE 2

| Sample | Turbidity Point (hours) |
|---|---|
| Product I | 8-12 |
| Product II | 20-24 |
| Product III | 140-155 |

EXAMPLE 5

Water Repellency and Gloss

Products I, II and III were diluted at a 1:10 ratio in water. The respective solutions were applied on cement sheets, sand stones, concrete and brick. Water repellency was determined based on the observed beading effect for each solution, wherein the beading effect of each solution was assigned a value from 1 to 5. A value of 1 represents a flat drop (i.e. low repellency) and a value of 5 represents an almost circular drop (i.e. high repellency). Product III (i.e. containing a transesterified organosilicon) exhibited the best beading effect or roll-off effect demonstrating the improved hydrophobicity or water repellency. The results are summarized in Table-3.

TABLE 3

| | Relative water Repellency* | | |
|---|---|---|---|
| Substrate | Product I | Product II | Product III |
| Brick | 3 | 3 | 5 |
| Sand stone | 3-4 | 3-4 | 4 |
| Concrete | 3-4 | 3-4 | 5 |
| Cement sheet | 3 | 3 | 4 |

*Water repellency based on the observed beading effect, wherein a value of 1 represents a flat drop and a value of 5 represents an almost circular drop.

Additionally, the compositions were evaluated for gloss, wherein no gloss was assigned a value of zero and a high gloss was assigned a value of five. The gloss of a composition is an indication of its degree of surface penetration and intermolecular condensation. In particular, a composition exhibiting reduced gloss is indicative of good substrate penetration and reduced intermolecular condensation. Unlike Products I and II, Product III (i.e. containing a transesterified organosilicon) exhibited minimum gloss thus indicating that the product has penetrated into the substrate and intermolecular condensation has been minimized. The results are summarized on Table-4.

TABLE 4

| Sample | Surface appearance* |
|---|---|
| Product (I) | 2 |
| Product (II) | 2 |
| Product (III) | 0 |

*Surface appearance Scale 0-5, 5 = high gloss, 0 = no gloss

EXAMPLE 6 iso-butyl(2-hydroxyethoxy)diethoxysilane

A two liter, three-necked flask equipped with a condenser, stirrer, thermometer and a distillation head, was charged with 360 grams (six moles) of ethylene glycol. To this, 220 grams (1 mole) of isobutyltriethoxysilane was added. The mixture was slowly heated to 100° C. and held for one hour. The temperature was raised to 120° C. and slowly vacuum was applied. The resulting transesterification reaction liberated ethanol which was removed and condensed. After approximately 46 g of ethanol (1 mole) was collected, vacuum was released and cooling applied. The average structure of the components of the crude product mixture was isobutyl(2-hydroxyethoxy)diethoxysilane: $(CH_3CH_2O)_2(OHCH_2CH_2O)SiC_4H_9$.

EXAMPLE 7

Vinyl(2-hydroxyethoxy)dimethoxysilane (hereinafter "Product IV")

A two liter, three-necked flask equipped with a condenser, stirrer, thermometer and a distillation head, was charged with 300 grams (six moles) of ethylene glycol. To this, 150 grams (1 mole) of Vinyltrimethoxysilane was added. The mixture was slowly heated to 80° C. and held for one hour. The temperature was then raised to 120° C. and slowly vacuum was applied. The transesterification reaction liberated methanol which was removed and condensed. After approximately 30 g of methanol (1 mole) was collected, vacuum was released and cooling applied. The average structure of the components of the crude product mixture was Vinyl(2-hydroxyethoxy)dimethoxysilane: $(CH_3O)_2(OHCH_2CH_2O)SiCH=CH_2$ (i.e. Product IV).

EXAMPLE 8

Flash Point Evaluation

Product IV was subjected to flash point test. The results are summarized in the Table-5. Samples were then heated to 80° C. for 4 days to simulate long storage life and then subjected to a second flash point determination. The results are summarized in Table-5. The data provided in Table-5 demonstrates that Product IV, including a transesterified organosilicon, did not exhibit any reduction in flash point upon aging at 80° C. for four days.

TABLE 5

| Sample | Flash Point* (° C.) | Flash Point (° C.) after Aging* |
|---|---|---|
| 40% Vinyltrimethoxysilane in ethylene glycol | 100 | 25 |
| 40% Product IV in ethylene glycol | 105 | 105 |

*Flash Points measured using Pensky-Martin Closed-cup

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A transesterified ionic organosilicon compound selected from the group consisting of:

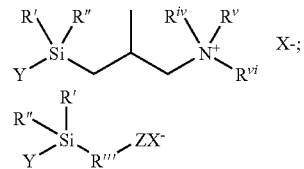

where in each formula:

Y is $(OCH_2CH_2)_nOH$ radical where n has a value of one through ten, or $[OC_3H_6]_nOH$ (propylene glycol) radical where n has a value of one through ten, or $[C_3H_7O_3]$, (glycerol) radical;

R' is an alkyl radical including one to three carbons, or $(OCH_2CH_2)_nOH$ radical where n has a value of one through ten, or $[OC_3H_5]_nOH$ (propylene glycol) radical where n has a value of one through ten, or $[C_3H_7O_3]$ (glycerol) radical, or $[O(CH_2)_mCH_3]$ radical where m has a value of 0, 1, 2 or 3, or $(CH_3OCH_2CH_2O)$ radical, or $(CH_3CH_2OCH_2CH_2O)$ radical; R" is an alkyl radical including one to three carbons, or $[O(CH_2)_mCH_3]$ radical where m has value 0, 1, 2 or 3 or $(CH_3OCH_2CH_2O)$ radical, or $(CH_3CH_2OCH_2CH_2O)$ radical; R''' is an alkylene group including one to four carbon atoms; $R^{iv}$, $R^v$ and $R^{vi}$ are alkyl groups including one to twenty two carbon atoms wherein at least one such group is larger than eight carbon atoms, $—CH_2C_6H_5$, $—CH_2CH_2OH$, $—CH_2OH$, and $=(CH_2)_xNHC(O)R^{vii}$ wherein x has a value of from two to ten and $R^{vii}$ is a perfluoroalkyl radical having one to twelve carbon atoms; X is chloride, bromide, fluoride, iodide, acetate or tosylate; and Z is a positively charged aromatic pyridinium ring of formula $C_5H_5N^+$.

2. A transesterified ionic organosilicon according to claim 1, wherein the ionic organosilicon compound is selected from the group consisting of:

(i) 3-[(2-hydroxyethoxy)dimethoxysilyl]2-methylpropyldimethyloctadecyl ammonium chloride;

(ii) 3-[di(2-hydroxyethoxy)methoxysilyl]2-methylpropyldimethyloctadecyl ammonium chloride (iii) 3-[(2-hydroxyethoxy)diethoxysilyl]2-methylpropyldimethyloctadecyl ammonium chloride; and (viii) 3-[di(2-hydroxyethoxy)ethoxysilyl]2-methylpropyldimethyloctadecyl ammonium chloride.

3. An aqueous-based composition consisting essentially of at least one transesterified ionic organo silicon compound of claim 1.

4. The aqueous-based composition of claim 3, wherein said composition comprises only one transesterified ionic organosilicon compound.

5. The aqueous-based composition of claim 4, wherein said transesterified ionic organosilicon compound is 3-[(2-hydroxyethoxy)dimethoxysilyl]2-methylpropyldimethyloctadecyl ammonium chloride.

6. The aqueous-based composition of claim 4, wherein said transesterified ionic organosilicon compound is 3-[di(2-hydroxyethoxy)methoxysilyl]2-methylpropyldimethyloctadecyl ammonium chloride.

7. The aqueous-based composition of claim 4, wherein said transesterified ionic organosilicon compound is 3-[(2-hydroxyethoxy)diethoxysilyl]2-methylpropyldimethyloctadecyl ammonium chloride.

8. The aqueous-based composition of claim 4, wherein said transesterified ionic organosilicon compound is 3-[di(2-hydroxyethoxy)ethoxysilyl]2-methylpropyldimethyloctadecyl ammonium chloride.

9. The aqueous-based composition of claim 4, wherein said one transesterified ionic organosilicon compound comprises between about 0.1 to about 10 weight percent of said aqueous-based composition.

* * * * *